US005739392A

United States Patent [19]

Tanimoto et al.

[11] Patent Number: 5,739,392
[45] Date of Patent: Apr. 14, 1998

[54] PROCESS FOR PRODUCTION OF ACRYLIC ACID

[75] Inventors: Michio Tanimoto; Ichiro Mihara; Tatsuya Kawajiri, all of Himeji, Japan

[73] Assignee: Nippon Shokubai Co., Ltd., Osaka, Japan

[21] Appl. No.: 557,353

[22] Filed: Nov. 13, 1995

[30] Foreign Application Priority Data

| Nov. 14, 1994 | [JP] | Japan | 6-279357 |
| Nov. 14, 1994 | [JP] | Japan | 6-279358 |
| Nov. 25, 1994 | [JP] | Japan | 6-291116 |

[51] Int. Cl.$^6$ .................................................. C07C 51/235
[52] U.S. Cl. ................................................................ 562/535
[58] Field of Search .................................................. 562/535

[56] References Cited

U.S. PATENT DOCUMENTS

| Re. 29,901 | 2/1979 | Wada et al. ............................ 252/443 |
| 3,867,438 | 2/1975 | Hensel et al. ........................ 260/530 N |
| 3,886,092 | 5/1975 | Wada et al. ............................ 252/443 |
| 3,997,600 | 12/1976 | Ferlazzo et al. ................... 260/530 N |
| 4,405,498 | 9/1983 | Ebner ...................................... 252/243 |
| 5,177,260 | 1/1993 | Kawajiri et al. .................... 562/535 |

FOREIGN PATENT DOCUMENTS

| 0 427 508 A1 | 5/1991 | European Pat. Off. |
| 0427508 | 5/1991 | European Pat. Off. |
| 1924496 | 11/1969 | Germany. |
| 2337510 | 10/1974 | Germany. |
| 50-25914 | 8/1975 | Japan. |

OTHER PUBLICATIONS

Heterogeneous Catalytic Oxidation of Acrolein to Acrylic Acid: Mechanism and Catalysts, T.V. Andrushkevich, Catal. Rev.-Sci. Eng., 35(2), 213–259/1993.

*Primary Examiner*—Gary Geist
*Assistant Examiner*—Rosalynd Keys
*Attorney, Agent, or Firm*—Sherman and Shalloway

[57] ABSTRACT

Acrylic acid can be produced efficiently by subjecting acrolein to catalytic gas-phase oxidation in the presence of a molybdenum/vanadium-based oxide catalyst prepared by using particular substances as the raw materials of the individual metal elements constituting the catalyst. A preferable example of such a catalyst is prepared by using, as the raw materials of vanadium, ammonium metavanadate and at least one vanadium oxide in which the valency of vanadium is larger than 0 but smaller than 5; as the raw material of copper, copper nitrate; and, as at least part of the raw material(s) of antimony, at least one antimony oxide in which the valency of antimony is larger than 0 but smaller than 5.

13 Claims, No Drawings

PROCESS FOR PRODUCTION OF ACRYLIC ACID

The present invention relates to a process for producing acrylic acid. More particularly, the present invention relates to a process for producing acrylic acid by subjecting acrolein or an acrolein-containing gas to catalytic gas-phase oxidation with molecular oxygen or a molecular oxygen-containing gas in the presence of a molybdenum/vanadium-based oxide catalyst prepared under particular conditions.

Various improved catalysts were proposed for efficient production of acrylic acid by catalytic gas-phase oxidation of acrolein. Most of them are molybdenum/vanadium-based catalysts containing molybdenum and vanadium as main components.

Some of the hitherto-proposed molybdenum/vanadium-based catalysts are at a fairly high level with respect to the yield of acrylic acid when viewed from an industrial production standpoint, and are actually used in industrial production of acrylic acid. Conventional molybdenum/vanadium-based catalysts, however, are not sufficiently satisfactory in view of the performance stability allowing for high yield of acrylic acid over a long period. Thus, it has been desired to develop a molybdenum/vanadium-based catalyst showing a long-term performance stability in production of acrylic acid by oxidation of acrolein.

An approach to the development of such a molybdenum/vanadium-based catalyst includes a study on the improvement of catalyst preparation process. In Japanese Patent Publication No. 25914/1975, for example, it is disclosed that by using an organic acid (e.g. oxalic acid) in catalyst preparation process, the oxidation state of catalyst is controlled, or a molybdenum-vanadium compound is formed. In this improved catalyst preparation process, however, a heat, which is generated by the decomposition of the organic acid in the heating and firing step of catalyst, deteriorates the performance of the catalyst obtained; moreover, when the resulting catalyst is used for oxidation of acrolein over a long period, the effect of the organic acid used in catalyst preparation process is difficult to maintain; therefore, the catalyst prepared by the above process is not satisfactory in acrylic acid yield and catalyst life when applied in industry.

The object of the present invention is to (1) develop a molybdenum/vanadium-based catalyst for acrylic acid production, represented by the following general formula (I)

$$Mo_aV_bW_cCu_dX_eY_fZ_gO_h \qquad (I)$$

(wherein the individual elements and their proportions are described later), which is excellent in activity, selectivity and life and which shows stable performance over a long period of time and (2) provide a process for producing acrylic acid at a high yield over a long period of time by subjecting acrolein or an acrolein-containing gas to catalytic gas-phase oxidation with molecular oxygen or a molecular oxygen-containing gas in the presence of the above-mentioned molybdenum/vanadium-based catalyst.

It is reported in T. V. ANDRUSHKEVICH, CATAL. REV.-SCI. ENG., 35, p. 213 (1993) that in molybdenum/vanadium-based catalysts such as represented by the above general formula (I), the active compound is $VMo_3O_{11}$; with the progress of oxidation of acrolein, this vanadium-molybdenum compound (hereinafter referred to as "vanadium-molybdenum active compound" in some cases) undergoes modification, resulting in the deterioration of catalyst; and when most of vanadium has been converted to a compound (e.g. $V_2O_5$) in which the valency of vanadium is 5, the selectivity of acrylic acid from acrolein is reduced remarkably.

The present inventors examined the property changes of molybdenum/vanadium-based catalysts, for example, the changes in surface area and pore volume and further, by using X-ray diffractometry, etc., compared the differences in physical and chemical properties between used catalyst of reduced activity and unused catalyst. As a result, the present inventors found out that when a molybdenum-vanadium-based catalyst is measured for X-ray pattern, the peak intensity appearing at d=4.00 Å has a relation to the performance of the catalyst and its change with time. According to the above-mentioned literature, the peak at d=4.00 Å is assigned to the vanadium-molybdenum active compound ($VMo_3O_{11}$).

Specific description is made below on a molybdenum/vanadium-based catalyst having a catalyst composition (an atomic ratio when oxygen is excluded) of $Mo_{12}V_5W_1Cu_{2.2}Sr_{0.5}$. This fresh catalyst and the used catalyst of reduced performance obtained when the fresh catalyst was subjected to catalytic gas-phase oxidation of acrolein continuously for 8,000 hours, were measured for surface area by BET method and pore volume. Their surface areas were 2.6 m²/g and 2.4 m²/g, respectively, and were not much different. Their pore volumes were 0.22 cc/g and 0.21 cc/g, respectively, and were not much different, either. In contrast, when the fresh and used catalysts were measured, by X-ray diffractometry, for peak at d=4.00 Å (assigned to the vanadium-molybdenum active compound) and peak at d=4.38 Å (assigned to $V_2O_5$, a five-valency vanadium compound), the intensity of the peak at d=4.00 Å was very low at 65 in the used (8,000 hours) catalyst when that of the fresh catalyst was taken as 100. Thus, it was found that the catalytic activity of the catalyst examined has a strong relation to the intensity of the vanadium-molybdenum active compound having a peak at d=4.00 Å and that one reason for reduction in catalytic activity during catalyst use is decrease of a crystal phase having a peak at d=4.00 Å.

Hence, the present inventors made an extensive study on the formation of the vanadium-molybdenum active compound having a peak at d=4.00 Å. As a result, the present inventors found out that a catalyst obtained by using, as the raw materials of vanadium and copper, ammonium metavanadate and copper nitrate, respectively, and replacing part of the ammonium metavanadate and/or the copper nitrate with a low-valency vanadium oxide and/or a low-valency copper oxide, or a catalyst obtained by using, in addition to the above raw materials, even a low-valency antimony oxide and/or a low-valency tin oxide, shows an increased peak intensity at d=4.00 Å assigned to the vanadium-molybdenum active compound and a decreased peak intensity at d=4.38 Å assigned to $V_2O_5$, and that the catalyst obtained as above has an improved catalytic activity and can show stable performance over a long period of time. The present invention has been completed based on the finding.

According to the present invention there is provided a process for producing acrylic acid by subjecting acrolein or an acrolein-containing gas to gas-phase oxidation with molecular oxygen or a molecular oxygen-containing gas in the presence of a molybdenum/vanadium-based oxide catalyst represented by the following general formula (I):

$$Mo_aV_bW_cCu_dX_eY_fZ_gO_h \qquad (I)$$

(wherein Mo is molybdenum; V is vanadium; W is tungsten; Cu is copper; X is at least one element selected from antimony and tin; Y is at least one element selected from magnesium, calcium, strontium and barium; Z is at least one element selected from titanium, zirconium and cerium; O is oxygen; a, b, c, d, e, f, g and h are the atom numbers of Mo, V, W, Cu, X, Y and Z, respectively, with a proviso that when a is 12, $2 \leq b \leq 14$, $0 \leq c \leq 12$, $0 < d \leq 6$ (preferably $0.01 \leq d \leq 6$), $0 \leq e \leq 5$ (preferably $0 < e \leq 5$, more preferably $0.01 \leq e \leq 5$), $0 \leq f \leq 3$ and $0 \leq g \leq 10$; and h is a number determined by the oxidation states of the individual elements other than O), in which process the molybdenum/vanadium-based oxide catalyst is produced by using the following substances as the raw materials of vanadium, copper, antimony and tin: when the molybdenum/vanadium-based oxide catalyst contains neither antimony nor tin, that is, when $e=0$, (A) the raw materials of vanadium are ammonium metavanadate and at least one vanadium oxide in which the valency of vanadium is larger than 0 but smaller than 5, and the raw material of copper is copper nitrate, or (B) the raw material of vanadium is ammonium metavanadate, and the raw materials of copper are copper nitrate and at least one copper oxide in which the valency of copper is larger than 0 but smaller than 2, or (C) the raw materials of vanadium are ammonium metavanadate and at least one vanadium oxide in which the valency of vanadium is larger than 0 but smaller than 5, and the raw materials of copper are copper nitrate and at least one copper oxide in which the valency of copper is larger than 0 but smaller than 2; and when the molybdenum/vanadium-based oxide catalyst contains antimony and/or tin, that is, when $0 < e \leq 5$, (D) the raw materials of vanadium are ammonium metavanadate and at least one vanadium oxide in which the valency of vanadium is larger than 0 but smaller than 5, the raw material of copper is copper nitrate, and at least part of the raw material(s) of antimony is at least one antimony oxide in which the valency of antimony is larger than 0 but smaller than 5, or (E) the raw materials of vanadium are ammonium metavanadate and at least one vanadium oxide in which the valency of vanadium is larger than 0 but smaller than 5, the raw material of copper is copper nitrate, and at least part of the raw material(s) of tin is at least one tin oxide in which the valency of tin is larger than 0 but smaller than 4, or (F) the raw materials of vanadium are ammonium metavanadate and at least one vanadium oxide in which the valency of vanadium is larger than 0 but smaller than 5, the raw material of copper is copper nitrate, at least part of the raw material(s) of antimony is at least one antimony oxide in which the valency of antimony is larger than 0 but smaller than 5, and at least part of the raw material(s) of tin is at least one tin oxide in which the valency of tin is larger than 0 but smaller than 4, or (G) the raw material of vanadium is ammonium metavanadate, the raw materials of copper are copper nitrate and at least one copper oxide in which the valency of copper is larger than 0 but smaller than 2, and at least part of the raw material(s) of antimony is at least one antimony oxide in which the valency of antimony is larger than 0 but smaller than 5, or (H) the raw material of vanadium is ammonium metavanadate, the raw materials of copper are copper nitrate and at least one copper oxide in which the valency of copper is larger than 0 but smaller than 2, and at least part of the raw material(s) of tin is at least one tin oxide in which the valency of tin is larger than 0 but smaller than 4, or (I) the raw material of vanadium is ammonium metavanadate, the raw materials of copper are copper nitrate and at least one copper oxide in which the valency of copper is larger than 0 but smaller than 2, at least part of the raw material(s) of antimony is at least one antimony oxide in which the valency of antimony is larger than 0 but smaller than 5, and at least part of the raw material(s) of tin is at least one tin oxide in which the valency of tin is larger than 0 but smaller than 4, or (J) the raw materials of vanadium are ammonium metavanadate and at least one vanadium oxide in which the valency of vanadium is larger than 0 but smaller than 5, the raw materials of copper are copper nitrate and at least one copper oxide in which the valency of copper is larger than 0 but smaller than 2, and at least part of the raw material(s) of antimony is at least one antimony oxide in which the valency of antimony is larger than 0 but smaller than 5, or (K) the raw materials of vanadium are ammonium metavanadate and at least one vanadium oxide in which the valency of vanadium is larger than 0 but smaller than 5, the raw materials of copper are copper nitrate and at least one copper oxide in which the valency of copper is larger than 0 but smaller than 2, and at least part of the raw material(s) of tin is at least one tin oxide in which the valency of tin is larger than 0 but smaller than 4, or (L) the raw materials of vanadium are ammonium metavanadate and at least one vanadium oxide in which the valency of vanadium is larger than 0 but smaller than 5, the raw materials of copper are copper nitrate and at least one copper oxide in which the valency of copper is larger than 0 but smaller than 2, at least part of the raw material(s) of antimony is at least one antimony oxide in which the valency of antimony is larger than 0 but smaller than 5, and at least part of the raw material(s) of tin is at least one tin oxide in which the valency of tin is larger than 0 but smaller than 4, or (M) the raw material of vanadium is ammonium metavanadate and part thereof is used in the form of a complex with an antimony compound in which the valency of antimony is larger than 0 but smaller than 5, and the raw material of copper is copper nitrate, or (N) the raw material of vanadium is ammonium metavanadate and part thereof is used in the form of a complex with a tin compound in which the valency of tin is larger than 0 but smaller than 4, and the raw material of copper is copper nitrate, or (O) the raw material of vanadium is ammonium metavanadate and part thereof is used in the form of a complex with (1) an antimony compound in which the valency of antimony is larger than 0 but smaller than 5 and (2) a tin compound in which the valency of tin is larger than 0 but smaller than 4, and the raw material of copper is copper nitrate.

In the present invention, a molybdenum/vanadium-based oxide catalyst prepared under one of the conditions (A) to (L) of the conditions (A) to (O) is used more preferably. In other words, in a preferred embodiment of the present invention, acrylic acid is produced by oxidation of acrolein using (1) a catalyst prepared under the condition (A), (B) or (C), or using (2) a catalyst prepared under the condition (D), (E), (F), (G), (H), (I), (J), (K) or (L), i.e. a catalyst prepared using the raw materials (A), (B) or (C) plus the raw material(s) of antimony and/or the raw material(s) of tin.

In the present invention, a molybdenum/vanadium-based oxide catalyst prepared under one of the conditions (D) to (L) of the conditions (A) to (L) is used particularly preferably. Therefore, in a more preferred embodiment of the present invention, acrylic acid is produced by oxidation of acrolein using a molybdenum/vanadium-based oxide catalyst prepared under the condition (D), (E), (F), (S), (H), (I), (J), (K) or (L).

It is not clear why the molybdenum/vanadium-based oxide catalyst represented by general formula (I), prepared according to the process of the present invention is superior in activity, selectivity and life. It is, however, presumed that when particular low-valency metal oxides as mentioned above are used as raw materials, the oxides react with each other and, as a result, the oxidation states of individual catalyst elements, particularly vanadium are controlled and the formation of the above-mentioned vanadium-molybdenum active compound is promoted.

Next, description is made on the raw material(s) of each catalyst element, used in preparation of the catalyst of the present invention.

When a Catalyst of e=0 is Prepared Under the Condition (A), (B) or (C)

Raw Material(s) of molybdenum (Mo):

Ammonium paramolybdate, molybdic acid, molybdenum oxide, etc. can be used singly or in admixture of two or more of them.

Raw Material(s) of tungsten (W):

Ammonium paratunstate, tungstic acid, tungsten oxide, etc. can be used singly or in admixture of two or more of them.

Raw Material(s) of vanadium (V):

Ammonium metavanadate, or a combination of ammonium metavanadate and a vanadium oxide in which the valency of vanadium is larger than 0 but smaller than 5, is used, The vanadium oxide in which the valency of vanadium is larger than 0 but smaller than 5 and which is used in combination with ammonibrm metavanadate (in other words, is used in place of part of ammonium metavanadate), includes vanadium monoxide, vanadium dioxide and vanadium trioxide. These can be used singly or in admixture of two or more of them.

The vanadium oxide is used desirably in such an amount as to satisfy (vanadium in vanadium oxide,)/(total vanadium) (atomic ratio)=0.01/1 to 0.5/1, preferably 0.03/1 to 0.3/1.

Raw material(s) of copper (Cu):

Copper nitrate, or a combination of copper nitrate and a copper oxide in which the valency of copper is larger than 0 but smaller than 2, is used.

The copper oxide in which the valency of copper is larger than 0 but smaller than 2 and which is used in combination with copper nitrate (in other words, is used in place of part of copper nitrate), includes cuprous oxide.

The copper oxide is used desirably in such an amount as to satisfy (copper in copper oxide)/(total copper) (atomic ratio)=0.01/1 to 0.5/1, preferably 0.03/1 to 0.3/1.

Raw material(s) of Y component:

A nitrate, carbonate, ammonium salt, sulfate, etc. of magnesium, calcium, strontium or barium can be used singly or in admixture of two or more of them.

Raw material(s) of Z component:

A nitrate, carbonate, ammonium salt, sulfate, hydroxide, oxide, etc. of titanium, zirconium or cerium can be used singly or in admixture of two or more of them.

When a Catalyst of $0<e\leq5$ is Prepared Under One of the Conditions (D) to (L)

Raw materials of molybdenum, tungsten, vanadium, copper, Y component and Z component:

The same raw material compounds as mentioned for the catalyst of e=0 can be used.

Raw Material(s) of Antimony (X Component):

As at least part of the antimony raw material(s), at least one antimony oxide in which the valency of antimony is larger than 0 but smaller than 5, is used. Antimony compound(s) which can be used in combination with the antimony oxide, include(s) a nitrate, ammonium salt, sulfate, etc. of antimony. These compounds can be used singly or in admixture of two or more of them.

That is, as the raw material(s) of antimony, there can be used the antimony oxide alone or a combination of the antimony oxide and other antimony compound(s) mentioned above.

The antimony oxide in which the valency of antimony is larger than 0 but smaller than 5 and which can be used as part or the whole of the antimony raw material(s), includes antimony trioxide and antimony tetraoxide. These can be used singly or in admixture.

Raw material(s) of tin (X component):

As at least part of the tin raw material(s), at least one tin oxide in which the valency of tin is larger than 0 but smaller than 4, is used. Tin compound(s) which can be used in combination with the tin oxide, include(s) a nitrate, ammonium salt, sulfate, hydroxide, etc. of tin. These compounds can be used singly or in admixture of two or more of them.

That is, as the raw material(s)of tin, there can be used the tin oxide alone or a combination of the tin oxide and other tin compound(s) mentioned above.

The tin oxide in which the valency of tin is larger than 0 but smaller than 4 and which can be used as part or the whole of the tin raw material(s), includes stannous oxide.

When the vanadium oxide is used as part of the ammonium metavanadate, the vanadium oxide is used desirably in such an amount that the vanadium atoms of the vanadium oxide become 0.1–45%, preferably 1–30% of the total vanadium atoms. When the copper oxide is used as part of the copper nitrate, the copper oxide is used desirably in such an amount that the copper atoms of the copper oxide become 0.1–45%, preferably 1–30% of the total copper atoms.

The antimony oxide used as part or the whole of the raw materials of antimony is used desirably in such an amount that the antimony atoms of the antimony oxide become 10–100%, preferably 30–100% of the total antimony atoms. The tin oxide used as part or the whole of the raw materials of tin is used desirably in such an amount that the tin atoms of the tin oxide become 10–100%, preferably 30–100% of the total tin atoms.

While the amount of each of the vanadium oxide, the copper oxide, the antimony oxide and the tin oxide used is as mentioned above, the total amount of these metal oxides used is desirably such that the total metal atoms thereof become 1–50%, preferably 2–45% of the total vanadium atoms.

When a Catalyst of 0<e≦5 is Prepared Under the Conditions (M), (N) or (O)

Raw materials of molybdenum, tungsten, Y component and Z component:

The same raw material compounds as mentioned for the catalyst of e=0 can be used.

Raw materials of vanadium:

Ammonium metavanadate is used, and at least part of the ammonium metavanadate is used as a complex with a low-valency X compound(s) mentioned later, i.e. a V-X complex (specifically, a V-Sb complex or a V-Sn complex or a V-Sb-Sn complex).

The amount of the ammonium metavanadate used for formation of the V-X complex may be 1–50% by weight, preferably 2–40% by weight of the total ammonium metavanadate amount used.

Raw material of copper:

Copper nitrate is used.

Raw material(s) of antimony (X component):

In the formation of the above-mentioned V-Sb complex, an antimony compound in which the valency of antimony is larger than 0 but smaller than 5, is used. Typical examples of this low-valency antimony compound are antimony trichloride, antimony oxychloride, antimony bromide, antimony trioxide, antimony tetraoxide, etc. These compounds can be used singly or in admixture of two or more of them.

As the antimony compound used in the form other than the V-Sb complex, there can be used ammonium salt, sulfate, oxides, etc. of antimony, and they can be used singly or in admixture of two or more of them. No antimony halide, however, can be used because it reduces the performance of the resulting molybdenum/vanadium-based oxide catalyst.

Raw material(s) of tin (X component):

In the formation of the above-mentioned V-Sn complex, a tin compound in which the valency of tin is larger than 0 but smaller than 4, is used. Typical examples of this low-valency tin compound are stannous chloride, stannous sulfate, tin acetate, tin oxalate, stannous hydroxide, stannous oxide, etc. These compounds can be used singly or in admixture of two or more of them.

As the tin compound used in the form other than the V-Sn complex, there can be used nitrate, ammonium salt, sulfate, oxides, etc. of tin, and they can be used singly or in admixture of two or more of them. No tin halide, however, can be used because it reduces the performance of the resulting molybdenum/vanadium-based oxide catalyst.

The further feature of the catalyst used in the present invention is that when the catalyst is subjected to X-ray diffractometry, the catalyst gives a high peak intensity at d=4.00 Å (the peak intensity at d=4.00 Å is hereinafter referred to as $d_{4.00}$) assigned to the vanadium-molybdenum phase of the catalyst and a low peak intensity at d=4.38 Å (the peak intensity at d=4.38 Å is hereinafter referred to as $d_{4.38}$) assigned to the $V_2O_5$ of the catalyst. When the ratio of the two peak intensities ($d_{4.38}/d_{4.00}$) is less than 0.07, a favorable catalytic activity is obtained. When the ratio is 0.06 or less, a more favorable catalytic activity is obtained; and when the ratio is 0–0.05, a particularly favorable catalytic activity is obtained. When the ratio is 0.07 or more, the amount of the vanadium-molybdenum phase is small and the resulting catalytic activity is low.

In the present invention, the catalyst desirably has a peak intensity retention of at least 80%, preferably at least 85% when the peak intensity retention is defined as percent of the peak intensity at d=4.00 Å, of used catalyst after 4,000-hour operation to the peak intensity at d=4.00 Å, of unused catalyst when the two catalysts are subjected to X-ray diffractometry. A catalyst having a peak intensity retention of lower than 80% contains a small amount of a active vanadium-molybdenum compound and consequently has low catalytic activity.

The method for preparation of the catalyst of the present invention is essentially the same as generally used in preparation of similar type catalysts, except that the present catalyst is prepared under one of the above-mentioned conditions (A) to (O). The present catalyst can be prepared by any of the evaporation-to-dryness method, granulation method, extrusion method, etc. all known hitherto.

The low-valency metal oxides may be added and dispersed at any step of catalyst preparation. In order to efficiently control the oxidation state of vanadium in catalyst preparation, the low-valency metal oxides are used preferably in small particles having an average particle diameter of 1–150 μm, preferably 5–100 μm.

In preparation of the present catalyst, it is possible to add inorganic fibers (e.g. glass fiber) and various whiskers, which are generally known to be effective for the improvement of catalyst strength and abrasion loss. In order to obtain a catalyst having properties of well-controlled ranges, it is also possible to add additives generally known as a binder for powder, such as ammonium nitrate, cellulose, starch, polyvinyl alcohol, stearic acid and the like.

The catalyst composition represented by general formula (I) may be used as it is, but is used preferably by being supported on an inert carrier such as alumina, silica-alumina, silicon carbide, titanium oxide, magnesium oxide, aluminum sponge, diatomaceous earth or the like.

With respect to the conditions employed when acrolein or an acrolein-containing gas is subjected to a catalytic gas-phase oxidation reaction using the present catalyst prepared by the above-mentioned method, there is no particular restriction. The reaction can be carried out using the process and conditions which are well known in similar reactions. The reaction can be conducted, for example, by contacting, with the present catalyst, a mixed gas comprising 1–15 % by volume, preferably 4–12% by volume of acrolein, 0.5–25% by volume, preferably 2–20% by volume of oxygen, 0–30% by volume, preferably 3–25% by volume of steam and 20–80% by volume, preferably 50–70% by volume of an inert gas (e.g. nitrogen) at a temperature of 180°–350° C., preferably 200°–330° C. at a pressure of normal pressure to 10 atm. (a reduced pressure may be used) at a space velocity (STP) of 500–20,000 $hr^{-1}$ preferably 1,000–10,000 $hr^{-1}$.

As the raw material gas to be contacted with the present catalyst, there can be used not only a mixed gas comprising acrolein, oxygen and an inert gas but also an acrolein-containing gas obtained by direct oxidation of propylene. When the latter gas is used, the oxidation products as by-products (e.g. acrylic acid, acetaldehyde and acetic acid), carbon oxides, propane, unreacted propylene, etc. contained in the acrolein-containing gas give no harm to the catalyst of the present invention.

The above catalytic gas-phase oxidation reaction can be carried out in a fixed bed or in a fluidized bed.

The molybdenum/vanadium-based catalyst of the present invention, having a high catalytic activity, can produce acrylic acid at a high yield.

The molybdenum/vanadium-based catalyst of the present invention, having a superior catalyst life, can maintain the excellent performance over a long period of time. As a result, even after the long-term use, the catalyst can produce acrylic acid at about the same high yield as at the reaction start, with no necessity of significant increase in reaction temperature.

The molybdenum/vanadium-based catalyst of the present invention, showing excellent performance even under high-load conditions, can produce acrylic acid at a high yield under such conditions.

The present invention is hereinafter described more specifically by way of Examples. However, the present invention is in no way restricted by these Examples.

In the Examples, acrolein conversion, acrylic acid selectivity and acrylic acid per-pass yield were determined by the following formulas.

Acrolein conversion (%)=(moles of acrolein reacted)÷(moles of acrolein fed)×100

Acrylic acid selectivity (%)=(moles of acrylic acid formed)÷(moles of acrolein reacted)×100

Acrylic acid per-pass yield (%)=(moles of acrylic acid formed)÷(moles of acrolein fed)×100

EXAMPLE 1

In 2,500 ml of water being heated and stirred were dissolved 350 g of ammonium paramolybdate, 106.3 g of ammonium metavanadate and 44.6 g of ammonium paratungstate. Separately, 87.8 g of copper nitrate was dissolved in 750 ml of water being heated and stirred, after which 5.9 g of cuprous oxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (1). The catalyst (1) had the following metal composition (expressed in terms of atomic ratio when oxygen excluded, the same applies hereinafter).

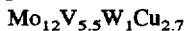
$Mo_{12}V_{5.5}W_1Cu_{2.7}$ 400 ml of the catalyst (1) was filled in a stainless steel-made U-tube having a diameter of 25 mm. A mixed gas comprising 4% by volume of acrolein, 4.5% by volume of oxygen, 25% by volume of steam and 66.5% by volume of nitrogen was introduced into the tube and subjected to an oxidation reaction at 255° C. for 2 seconds (a contact time). The results are shown in Table 1.

Separately, the catalyst (1) was subjected to X-ray diffractometry to measure its peak intensities at d=4.00 Å and d=4.38 Å, i.e. $d_{4.00}$ and $d_{4.38}$; and the latter peak intensity was reported in Table 1 as relative peak intensity when the former peak intensity was taken as 100.

Comparative Example 1

A catalyst (2) having the same composition as that of the catalyst (1) was prepared in the same manner as in Example 1 except that copper nitrate was used in place of the cuprous oxide used in Example 1. Then, an oxidation reaction was conducted in the same manner as in Example 1 except that the catalyst (2) was used in place of the catalyst (1). The results are shown in Table 1.

Separately, the catalyst (2) was subjected to X-ray diffractometry in the same manner as in Example 1 to measure its peak intensities at d=4.00 Å and d=4.38 Å, i.e. $d_{4.00}$ and $d_{4.38}$; and they were reported in Table 1 as relative peak intensities when the peak intensity of the catalyst (1) at d=4.00 Å was taken as 100.

Comparative Example 2

A catalyst (3) having the same composition as that of the catalyst (1) was prepared in the same manner as in Example 1 except that cupric oxide was used in place of the cuprous oxide used in Example 1. Then, an oxidation reaction was conducted in the same manner as in Example 1 except that the catalyst (3) was used in place of the catalyst (1). The results are shown in Table 1.

Separately, the catalyst (3) was subjected to X-ray diffractometry in the same manner as in Example 1 to measure its peak intensities at d=4.00 Å and d=4.38 Å, i.e. $d_{4.00}$ and $d_{4.38}$; and they were reported in Table 1 as relative peak intensities when the peak intensity of the catalyst (1) at d=4.00 Å was taken as 100.

TABLE 1

| Example No. | Catalyst No. | Acrolein conversion (mole %) | Acrylic acid yield (mole %) | Acrylic acid selectivity (mole %) | Relative peak intensity | | |
|---|---|---|---|---|---|---|---|
| | | | | | $d_{4.00}$ | $d_{4.38}$ | $d_{4.38}/d_{4.00}$ |
| Example 1 | (1) | 98.8 | 93.3 | 94.5 | 100 | 5 | 0.05 |
| Comparative Example 1 | (2) | 94.2 | 88.5 | 94.0 | 82 | 14 | 0.17 |
| Comparative Example 2 | (3) | 95.5 | 89.8 | 94.1 | 86 | 12 | 0.14 |

As is clear from the results of Table 1, when neither vanadium oxide having a vanadium valency larger than 0 but smaller than 5 nor copper compound having a copper valency larger than 0 but smaller than 2 is used (Comparative Example 1), or when a copper compound having a copper valency of 2 or larger is used (Comparative Example 2), the resulting catalyst has a low relative peak intensity at d=4.00 Å and low catalytic activity.

EXAMPLE 2

An oxidation reaction was conducted for 4,000 hours using the catalyst (1) under the same conditions as in Example 1. The results are shown in Table 2.

The used catalyst (1) after 4,000-hour reaction was subjected to X-ray diffractometry in the same manner as in Example 1 to measure its peak intensity at d=4.00 Å, and it was reported in Table 2 as relative peak intensity at d=4.00 Å when the peak intensity of the unused catalyst (1) at d=4.00 Å was taken as 100.

Comparative Example 3

An oxidation reaction was conducted in the same manner as in Example 2 except that the catalyst (2) was used in place of the catalyst (1). The results are shown in Table 2.

The used catalyst (2) after 4,000-hour reaction was subjected to X-ray diffractometry in the same manner as in Example 1 to measure its peak intensity at d=4.00 Å, and it

Comparative Example 4

An oxidation reaction was conducted in the same manner as in Example 2 except that the catalyst (3) was used in place of the catalyst (1). The results are shown in Table 2.

The used catalyst (3) after 4,000-hour reaction was subjected to X-ray diffractometry in the same manner as in Example 1 to measure its peak intensity at d=4.00 Å, and it was reported in Table 2 as relative peak intensity at d=4.00 Å when the peak intensity of the unused catalyst (1) at d=4.00 Å was taken as 100.

TABLE 2

| Example No. | Catalyst No. | Acrolein conversion (mole %) | Acrylic acid yield (mole %) | Acrylic acid selectivity (mole %) | Reduction of relative peak intensity at d = 4.00 Å |
|---|---|---|---|---|---|
| Example 2 | (1) | 97.8 | 92.4 | 94.5 | 90 |
| Comparative Example 3 | (2) | 92.7 | 87.2 | 94.1 | 70 |
| Comparative Example 4 | (3) | 94.1 | 88.5 | 94.1 | 73 |

*(Peak intensity at d = 4.00 Å of 4000 hrs used catalyst ) ÷ (Peak intensity at d = 4.00 Å of unused catalyst (1)) × 100

As is clear from the results of Table 2, the catalyst obtained by the present invention process is superior in catalyst life.

EXAMPLE 3

An oxidation reaction was conducted in the same manner as in Example 1 using the catalyst (1) except that the contact time was changed to 1.5 seconds. The results are shown in Table 3.

Comparative Example 5

An oxidation reaction was conducted in the same manner as in Example 3 except that the catalyst (2) was used in place of the catalyst (1). The results are shown in Table 3.

Comparative Example 6

An oxidation reaction was conducted in the same manner as in Example 3 except that the catalyst (3) was used in place of the catalyst (1). The results are shown in Table 3.

EXAMPLE 4

An oxidation reaction was conducted in the same manner as in Example 1 using the catalyst (1) except that the proportions of acrolein and nitrogen in raw material gas were changed to 5% by volume and 65.5% by volume, respectively. The results are shown in Table 3.

Comparative Example 7

An oxidation reaction was conducted in the same manner as in Example 4 except that the catalyst (2) was used in place of the catalyst (1). The results are shown in Table 3.

Comparative Example 8

An oxidation reaction was conducted in the same manner as in Example 4 except that the catalyst (3) was used in place of the catalyst (1). The results are shown in Table 3.

TABLE 3

| Example No. | Catalyst No. | Acrolein conversion (mole %) | Acrylic acid yield (mole %) | Acrylic acid selectivity (mole %) |
|---|---|---|---|---|
| Example 3 | (1) | 98.6 | 92.9 | 94.2 |
| Comparative Example 5 | (2) | 93.5 | 87.7 | 93.8 |
| Comparative Example 6 | (3) | 94.8 | 89.1 | 94.0 |
| Example 4 | (1) | 98.5 | 92.6 | 94.0 |
| Comparative Example 7 | (2) | 93.3 | 87.3 | 93.6 |
| Comparative Example 8 | (3) | 94.5 | 88.6 | 93.8 |

EXAMPLE 5

In 2,500 ml of water being heated and stirred were dissolved 350 g of ammonium paramolybdate, 116 g of ammonium metavanadate and 44.6 g of ammonium paratungstate. Separately, 87.8 g of copper nitrate was dissolved in 750 ml of water being heated and stirred, after which 8.2 g of cuprous oxide and 6.6 g of zirconium hydroxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (4). The catalyst (4) had the following metal composition.

$Mo_{12}V_6W_1Cu_{2.9}Zr_{0.25}$

An oxidation reaction was conducted in the same manner as in Example 1 except that the catalyst (4) was used in place of the catalyst (1). The results are shown in Table 4.

EXAMPLE 6

In 2,500 ml of water being heated and stirred were dissolved 350 g of ammonium paramolybdate, 96.6 g of ammonium metavanadate and 44.6 g of ammonium paratungstate. Separately, 87.8 g of copper nitrate was dissolved in 750 ml of water being heated and stirred, after which 1.2 g of cuprous oxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (5). The catalyst (5) had the following metal composition.

$Mo_{12}V_5W_1Cu_{2.3}$

An oxidation reaction was conducted in the same manner as in Example 1 except that the catalyst (5) was used in place of the catalyst (1). The results are shown in Table 4.

EXAMPLE 7

In 2,500 ml of water being heated and stirred were dissolved 350 g of ammonium paramolybdate, 106.3 g of ammonium metavanadate and 44.6 g of ammonium paratungstate. Thereto was added 6.9 g of vanadium dioxide. Separately, 87.8 g of copper nitrate and 26 g of titanium oxide were dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (6). The catalyst (6) had the following metal composition.

$Mo_{12}V_6W_1Cu_{2.2}Ti_2$

An oxidation reaction was conducted in the same manner as in Example 1 except that the catalyst (6) was used in place of the catalyst (1). The results are shown in Table 4.

EXAMPLE 8

In 2,500 ml of water being heated and stirred were dissolved 350 g of ammonium paramolybdate, 116 g of ammonium metavanadate and 44.6 g of ammonium paratungstate. Thereto was added 20.5 g of vanadium dioxide. Separately, 87.8 g of copper nitrate was dissolved in 750 ml of water being heated and stirred, after which 10 g of zirconium oxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (7). The catalyst (7) had the following metal composition.

$Mo_{12}V_{7.5}W_1Cu_{2.2}Zr_{0.5}$

An oxidation reaction was conducted in the; same manner as in Example 1 except that the catalyst: (7) was used in place of the catalyst (1). The results are shown in Table 4.

EXAMPLE 9

In 2,500 ml of water being heated and stirred were dissolved 350 g of ammonium paramolybdate, 96.6 g of ammonium metavanadate and 44.6 g of ammonium paratungstate. Thereto was added 2.5 g of vanadium trioxide. Separately, 87.8 g of copper nitrate was dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (8). The catalyst (8) had the following metal composition.

$Mo_{12}V_{5.7}W_1Cu_{2.2}$

An oxidation reaction was conducted in the same manner as in Example 1 except that the catalyst (8) was used in place of the catalyst (1). The results are shown in Table 4.

EXAMPLE 10

In 2,500 ml of water being heated and stirred were dissolved 350 g of ammonium paramolybdate, 96.6 g of ammonium metavanadate and 44.6 g of ammonium paratungstate. Thereto were added 6.9 g of vanadium dioxide and 1.1 g of vanadium monoxide. Separately, 87.8 g of copper nitrate was dissolved in 750 ml of water being heated and stirred, after which 28.4 g of cerium oxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (9). The catalyst (9) had the following metal composition.

$Mo_{12}V_{6.5}W_1Cu_{2.2}Ce_1$

An oxidation reaction was conducted in the same manner as in Example 1 except that the catalyst (9) was used in place of the catalyst (1). The results are shown in Table 4.

EXAMPLE 11

In 2,500 ml of water being heated and stirred were dissolved 350 g of ammonium paramolybdate, 106.3 g of ammonium metavanadate and 44.6 g of ammonium paratungstate. Thereto was added 4.1 g of vanadium dioxide. Separately, 87.8 g of copper nitrate was dissolved in 750 ml of water being heated and stirred, after which 2.4 g of cuprous oxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (10). The catalyst (10) had the following metal composition.

$Mo_{12}V_{5.8}W_1Cu_{2.4}$

An oxidation reaction was conducted in the same manner as in Example 1 except that the catalyst (10) was used in place of the catalyst (1). The results are shown in Table 4.

TABLE 4

| Example No. | Catalyst No. | Acrolein conversion (mole %) | Acrylic acid yield (mole %) | Acrylic acid selectivity (mole %) | Ratio of peak intensities ($d_{4.3\theta}/d_{4.00}$) |
|---|---|---|---|---|---|
| Example 5 | (4) | 98.5 | 92.8 | 94.2 | 0.05 |
| Example 6 | (5) | 99.0 | 93.9 | 94.8 | 0.05 |
| Example 7 | (6) | 99.2 | 93.7 | 94.5 | 0.03 |
| Example 8 | (7) | 98.7 | 93.8 | 95.0 | 0.04 |
| Example 9 | (8) | 98.9 | 93.0 | 94.0 | 0.05 |
| Example 10 | (9) | 99.1 | 93.6 | 94.4 | 0.03 |
| Example 11 | (10) | 98.8 | 96.8 | 94.9 | 0.04 |

EXAMPLE 12

Industrial propylene (purity: 94% or higher) was subjected to catalytic gas-phase oxidation in the presence of a molybdenum/bismuth-based catalyst to obtain a reaction mixture gas comprising 5% by volume of acrolein, 1.2% by volume of unreacted propylene and organic by-products, 4.5% by volume of oxygen, 20% by volume of steam and 69.3% by volume of a nitrogen-containing inert gas.

Successively, the reaction mixture gas was introduced into a reaction tube filled with the catalyst (1) and subjected to an oxidation reaction under the conditions of a temperature of 260° C. and a contact time of 2 seconds.

An acrolein conversion of 99.0%, an acrylic acid selectivity of 94.5% and an acrylic acid per-pass yield of 93.6% were obtained.

The above results confirmed that the catalyst produced by the present invention maintained a high activity and could produce acrylic acid from acrolein stably at a high yield.

EXAMPLE 13

In 2,500 ml of water being heated and stirred were dissolved 350 g of ammonium paramolybdate, 116 g of ammonium metavanadate and 44.6 g of ammonium paratungstate. Thereto was added 1.5 g of vanadium trioxide. Separately, 87.8 g of copper nitrate was dissolved in 750 ml of water being heated and stirred, after which 1.2 g of cuprous oxide and 29 g of antimony trioxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (11). The catalyst (11) had the following metal composition.

$Mo_{12}V_{6.1}W_1Cu_{2.3}Sb_{1.2}$ 400 ml of the catalyst (11) was filled in a stainless steel-made U-tube having a diameter of 25 mm. A mixed gas comprising 4.5% by volume of acrolein, 5% by volume of oxygen, 25% by volume of steam and 65.5% by volume of nitrogen was introduced into the tube and subjected to an oxidation reaction at 250° C. for a contact time of 2 seconds. The results are shown in Table 5.

Separately, the catalyst (11) was subjected to X-ray diffractometry to measure its peak intensities at d=4.00 Å and d=4.38 Å, i.e. $d_{4.00}$ and $d_{4.38}$; and the latter peak intensity was reported in Table 5 as relative peak intensity when the former peak intensity was taken as 100.

Comparative Example 9

A catalyst (12) was prepared in the same manner as in Example 13 except that vanadium pentoxide, cupric oxide and antimony pentoxide were used in place of the vanadium dioxide, cuprous oxide and antimony trioxide used in Example 13. An oxidation reaction was conducted in the same manner as in Example 13 except that the catalyst (12) was used in place of the catalyst (11). The results are shown in Table 5.

Separately, the catalyst (12) was subjected to X-ray diffractometry in the same manner as in Example 13 to measure its peak intensities at d=4.00 Å and d=4.38 Å, i.e. $d_{4.00}$ and $d_{4.38}$; and they were reported in Table 5 as relative peak intensities when the peak intensity of the catalyst (11) at d=4.00 Å was taken as 100.

Comparative Example 10

A catalyst (13) was prepared in the same manner as in Example 13 except that vanadium trioxide and cuprous oxide were used in place of the antimony trioxide used in Example 13. The catalyst (13) had the following metal composition.

$Mo_{12}V_{6.7}W_1Cu_{2.9}$

An oxidation reaction was conducted in the same manner as in Example 13 except that the catalyst (13) was used in place of the catalyst (11). The results are shown in Table 5.

Separately, the catalyst (13) was subjected to X-ray diffractometry in the same manner as in Example 13 to measure its peak intensities at d=4.00 Å and d=4.38 Å, i.e. $d_{4.00}$ and $d_{4.38}$; and they were reported in Table 5 as relative peak intensities when the peak intensity of the catalyst (11) at d=4.00 Å was taken as 100.

Comparative Example 11

A catalyst (14) was prepared in the same manner as in Example 13 except that antimony trioxide was used in place of the vanadium dioxide and cuprous oxide used in Example 13. The catalyst (14) had the following metal composition.

$Mo_{12}V_{6.7}W_1Cu_{2.2}Sb_{1.4}$

An oxidation reaction was conducted in the same manner as in Example 13 except that the catalyst (14) was used in place of the catalyst (11). The results are shown in Table 5.

Separately, the catalyst (14) was subjected to X-ray diffractometry in the same manner as in Example 13 to measure its peak intensities at d=4.00 Å and d=4.38 Å, i.e. $d_{4.00}$ and $d_{4.38}$; and they were reported in Table 5 as relative peak intensities when the peak intensity of the catalyst (11) at d=4.00 Å was taken as 100.

TABLE 5

| Example No. | Catalyst No. | Acrolein conversion (mole %) | Acrylic acid yield (mole %) | Acrylic acid selectivity (mole %) | Relative peak intensity | | |
|---|---|---|---|---|---|---|---|
| | | | | | $d_{4.00}$ | $d_{4.38}$ | $d_{4.38}/d_{4.00}$ |
| Example 13 | (11) | 98.8 | 94.4 | 95.5 | 100 | 1 | 0.01 |
| Comparative Example 9 | (12) | 95.4 | 89.5 | 93.8 | 79 | 12 | 0.15 |
| Comparative Example 10 | (13) | 95.9 | 89.2 | 93.0 | 84 | 15 | 0.18 |
| Comparative Example 11 | (14) | 96.2 | 90.6 | 94.2 | 86 | 8 | 0.09 |

EXAMPLE 14

An oxidation reaction was conducted for 8,000 hours using the catalyst (11) under the same conditions as in Example 13. Then, the product was collected and analyzed. The results are shown in Table 6.

The used catalyst (11) after 8,000-hour reaction was subjected to X-ray diffractometry in the same manner as in Example 13 to measure its peak intensity at d=4.00 Å, and it was reported in Table 6 as relative peak intensity at d=4.00 Å when the peak intensity of the unused catalyst (11) at d=4.00 Å was taken as 100.

Comparative Example 12

An oxidation reaction was conducted in the same manner as in Example 14 except that the catalyst (12) was used in place of the catalyst (11). The results are shown in Table 6.

The used catalyst (12) after 8,000-hour reaction was subjected to X-ray diffractometry in the same manner as in Example 13 to measure its peak intensity at d=4.00 Å, and it was reported in Table 6 as relative peak intensity at d=4.00 Å when the peak intensity of the unused catalyst (11) at d=4.00 Å was taken as 100.

TABLE 6

| Example No. | Catalyst No. | Acrolein conversion (mole %) | Acrylic acid yield (mole %) | Acrylic acid selectivity (mole %) | Relative peak intensity at d = 4.00 Å |
|---|---|---|---|---|---|
| Example 14 | (11) | 97.2 | 92.9 | 95.6 | 95 |
| Comparative Example 12 | (12) | 92.5 | 87.0 | 94.0 | 63 |

EXAMPLE 15

An oxidation reaction was conducted in the same manner as in Example 13 using the catalyst (11) except that the contact time was changed to 1.5 seconds. The results are shown in Table 7.

Comparative Example 13

An oxidation reaction was conducted in the same manner as in Example 15 except that the catalyst (12) was used in place of the catalyst (11). The results are shown in Table 7.

EXAMPLE 16

An oxidation reaction was conducted in the same manner as in Example 13 using the catalyst (11) except that the proportions of acrolein and nitrogen present in raw material gas were changed to 5.5% by volume and 64.5% by volume, respectively. The results are shown in Table 7.

Comparative Example 14

An oxidation reaction was conducted in the same manner as in Example 16 except that the catalyst (12) was used in place of the catalyst (11). The results are shown in Table 7.

TABLE 7

| Example No. | Catalyst No. | Acrolein conversion (mole %) | Acrylic acid yield (mole %) | Acrylic acid selectivity (mole %) |
|---|---|---|---|---|
| Example 15 | (11) | 98.6 | 94.1 | 95.4 |
| Comparative Example 13 | (12) | 95.0 | 89.0 | 93.7 |
| Example 16 | (11) | 98.4 | 93.7 | 95.2 |
| Comparative Example 14 | (12) | 94.7 | 88.5 | 93.5 |

EXAMPLE 17

In 2,500 ml of water being heated and stirred were dissolved 350 g of ammonium paramolybdate, 116 g of ammonium metavanadate and 44.6 g of ammonium paratungstate. Thereto was added 22 g of vanadium dioxide. Separately, 87.8 g of copper nitrate and 8.7 g of strontium nitrate were dissolved in 750 ml of water being heated and stirred, after which 2.4 g of antimony trioxide and 13 g of zirconium hydroxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (15). The catalyst (15) had the following metal composition.

$Mo_{12}V_{7.6}W_1Cu_{2.2}Sb_{0.1}Sr_{0.25}Zr_{0.5}$

An oxidation reaction was conducted in the same manner as in Example 13 except that the catalyst (15) was used in place of the catalyst (11). The results are shown in Table 8.

EXAMPLE 18

In 2,500 ml of water being heated and stirred were dissolved 350 g of ammonium paramolybdate, 116 g of ammonium metavanadate and 44.6 g of ammonium paratungstate. Thereto was added 2.7 g of vanadium dioxide. Separately, 87.8 g of copper nitrate and 10.6 g of magnesium nitrate were dissolved in 750 ml of water being heated and stirred, after which 2.4 g of antimony trioxide and 12.7 g of antimony tetraoxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (16). The catalyst (16) had the following metal composition.

$Mo_{12}V_{6.2}W_1Cu_{2.2}Sb_{0.6}Mg_{0.25}$

An oxidation reaction was conducted in the same manner as in Example 13 except that the catalyst (16) was used in place of the catalyst (11). The results are shown in Table 8.

EXAMPLE 19

In 2,500 ml of water being heated and stirred were dissolved 350 g of ammonium paramolybdate, 106 g of ammonium metavanadate and 44.6 g of ammonium paratungstate. Thereto were added 2.7 g of vanadium dioxide and 1.5 g of vanadium trioxide. Separately, 87.8 g of copper nitrate was dissolved in 750 ml of water being heated and stirred, after which 6 g of antimony trioxide and 13.2 g of titanium oxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (17). The catalyst (17) had the following metal composition.

$Mo_{12}V_{5.8}W_1Cu_{2.2}Sb_{0.25}Ti_1$

An oxidation reaction was conducted in the same manner as in Example 13 except that the catalyst (17) was used in place of the catalyst (11). The results are shown in Table 8.

EXAMPLE 20

In 2,500 ml of water being heated and stirred were dissolved 350 g of ammonium paramolybdate, 135 g of ammonium metavanadate and 44.6 g of ammonium paratungstate. Thereto was added 6.9 g of vanadium dioxide. Separately, 87.8 g of copper nitrate was dissolved in 750 ml of water being heated and stirred, after which 63.5 g of antimony tetraoxide and 20.4 g of zirconium oxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (18). The catalyst (18) had the following metal composition.

$Mo_{12}V_{7.5}W_1Cu_{2.2}Sb_{2.5}Zr_1$

An oxidation reaction was conducted in the same manner as in Example 13 except that the catalyst (18) was used in place of the catalyst (11). The results are shown in Table 8.

EXAMPLE 21

In 2,500 ml of water being heated and stirred were dissolved 350 g of ammonium paramolybdate, 116 g of ammonium metavanadate and 44.6 g of ammonium paratungstate. Separately, 87.8 g of copper nitrate and 19.5 g of calcium nitrate were dissolved in 750 ml of water being heated and stirred, after which 7 g of cuprous oxide and 9.6 g of antimony trioxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (19). The catalyst (19) had the following metal composition.

$Mo_{12}V_6W_1Cu_{2.8}Sb_{0.2}Ca_{0.5}$

An oxidation reaction was conducted in the same manner as in Example 13 except that the catalyst (19) was used in place of the catalyst (11). The results are shown in Table 8.

EXAMPLE 22

In 2,500 ml of water being heated and stirred were dissolved 350 g of ammonium paramolybdate, 96.6 g of ammonium metavanadate and 44.6 g of ammonium paratungstate. Separately, 87.8 g of copper nitrate and 10.8 g of barium nitrate were dissolved in 750 ml of water being heated and stirred, after which 0.6 g of cuprous oxide and 3.6 g of antimony trioxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (20). The catalyst (20) had the following metal composition.

$Mo_{12}V_5W_1Cu_{2.25}Sb_{0.15}Ba_{0.25}$

An oxidation reaction was conducted in the same manner as in Example 13 except that the catalyst (20) was used in place of the catalyst (11). The results are shown in Table 8.

EXAMPLE 23

In 2,500 ml of water being heated and stirred were dissolved 350 g of ammonium paramolybdate, 106 g of ammonium metavanadate and 44.6 g of ammonium paratungstate. Thereto was added 1.4 g of vanadium dioxide. Separately, 87.8 g of copper nitrate was dissolved in 750 ml of water being heated and stirred, after which 25.4 g of antimony tetraoxide was added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (21). The catalyst (21) had the following metal composition.

$Mo_{12}V_{5.6}W_1Cu_{2.2}Sb_1$

An oxidation reaction was conducted in the same manner as in Example 13 except that the catalyst (21) was used in place of the catalyst (11). The results are shown in Table 8.

EXAMPLE 24

In 2,500 ml of water being heated and stirred were dissolved 350 g of ammonium paramolybdate, 116 g of ammonium metavanadate and 44.6 g of ammonium paratungstate. Thereto was added 2.7 g of vanadium dioxide. Separately, 87.8 g of copper nitrate was dissolved in 750 ml of water being heated and stirred, after which 2.4 g of cuprous oxide and 11 g of stannous oxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (22). The catalyst (22) had the following metal composition.

$Mo_{12}V_{6.2}W_1Cu_{2.4}Sn_{0.5}$

An oxidation reaction was conducted in the same manner as in Example 13 except that the catalyst (22) was used in place of the catalyst (11). The results are shown in Table 8.

EXAMPLE 25

In 2,500 ml of water being heated and stirred were dissolved 350 g of ammonium paramolybdate, 116 g of ammonium metavanadate and 44.6 g of ammonium paratungstate. Thereto was added 1.5 g of vanadium trioxide. Separately, 87.8 g of copper nitrate was dissolved in 750 ml of water being heated and stirred, after which 1.2 g of cuprous oxide, 12 g of antimony trioxide arid 2.2 g of stannous oxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the; carrier, followed by firing at 400° C. for 6 hours, to obtain a catalyst (23). The catalyst (23) had the following metal composition.

$Mo_{12}V_{6.1}W_1Cu_{2.3}Sb_{0.5}Sn_{0.1}$

An oxidation reaction was conducted in the same manner as in Example 13 except that the catalyst (23) was used in place of the catalyst (11). The results are shown in Table 8.

EXAMPLE 26

In 2,500 ml of water being heated and stirred were dissolved 350 g of ammonium paramolybdate, 106 g of ammonium metavanadate and 44.6 g of ammonium paratungstate. Thereto was added 1.2 g of vanadium trioxide. Separately, 87.8 g of copper nitrate was dissolved in 750 ml of water being heated and stirred, after which 2.5 g of tin hydroxide, 4.4 g of stannous oxide and 14 g of cerium oxide were added thereto. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (24). The catalyst (24) had the following metal composition.

$Mo_{12}V_{5.6}W_1Cu_{2.2}Sn_{0.3}Ce_{0.5}$

An oxidation reaction was conducted in the same manner as in Example 13 except that the catalyst (24) was used in place of the catalyst (11). The results are shown in Table 8.

TABLE 8

| Example No. | Catalyst No. | Acrolein conversion (mole %) | Acrylic acid yield (mole %) | Acrylic acid selectivity (mole %) | Ratio of peak intensities ($d_{4.38}/d_{4.00}$) |
|---|---|---|---|---|---|
| Example 17 | (15) | 98.6 | 94.3 | 95.6 | 0.03 |
| Example 18 | (16) | 99.0 | 94.8 | 95.8 | 0 |
| Example 19 | (17) | 99.2 | 94.5 | 95.3 | 0.04 |
| Example 20 | (18) | 98.6 | 94.6 | 96.0 | 0.04 |
| Example 21 | (19) | 99.1 | 94.1 | 95.0 | 0.03 |
| Example 22 | (20) | 99.3 | 94.8 | 95.5 | 0 |
| Example 23 | (21) | 98.8 | 94.3 | 95.4 | 0.05 |
| Example 24 | (22) | 99.1 | 94.0 | 95.0 | 0.04 |
| Example 25 | (23) | 98.9 | 94.3 | 95.3 | 0.03 |
| Example 26 | (24) | 99.2 | 94.2 | 95.0 | 0.04 |

EXAMPLE 27

Industrial propylene (purity: 94% or higher) was subjected to catalytic gas-phase oxidation in the presence of a molybdenum/bismuth-based catalyst to obtain a reaction mixture gas comprising 5.5% by volume of acrolein, 1.3% by volume of unreacted propylene and organic by-products, 5% by volume of oxygen, 20% by volume of steam and 68.2% by volume of a nitrogen-containing inert gas.

Successively, the reaction mixture gas was introduced into a reaction tube filled with the catalyst (11) and subjected to an oxidation reaction under the conditions of temperature=255° C. and contact time=2 seconds.

An acrolein conversion of 99.1%, an acrylic acid selectivity of 95.4% and an acrylic acid per-pass yield of 94.5% were obtained based on an assumption that the propylene, propane, acrylic acid, acetic acid, etc. present in the reaction mixture gas introduced into the reaction tube did not take part in the oxidation reaction.

The above results confirmed that the catalyst produced by the present invention maintained a high activity and could produce acrylic acid from acrolein stably at a high yield.

EXAMPLE 28

[Preparation of V-Sb complex]

9.7 g of ammonium metavanadate was dissolved in 500 ml of water being heated and stirred. To the solution was added 18.8 g of antimony trichloride. The mixture was placed in a porcelain-made evaporator set on a hot water bath, and concentrated to dryness. The resulting solid was dried at 350° C. for 6 hours and then ground to obtain 20 g of a powder (A-1) of 150 µm or less. The powder (A-1) had the following metal composition (expressed in terms of atomic ratio when oxygen excluded, the same applies hereinafter).

$V_1Sb_1$

[Preparation of catalyst]

In 2,500 ml of water being heated and stirred were dissolved 350 g of ammonium paramolybdate, 106 g of ammonium metavanadate and 44.6 g of ammonium paratungstate. Thereto was added 20 g of the powder (A-1). Separately, 87.8 g of copper nitrate was dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (25). The catalyst (25) had the following metal composition.

$Mo_{12}V_6W_1Cu_{2.2}Sb_{0.5}$

[Oxidation reaction]

400 ml of the catalyst (25) was filled in a stainless steel-made U-tube having a diameter of 25 mm. A mixed gas comprising 4% by volume of acrolein, 4.5% by volume of oxygen, 25% by volume of steam and 66.5% by volume of nitrogen was introduced into the tube and subjected to an oxidation reaction at 250° C. for 2 seconds (a contact time). The results are shown in Table 9.

Separately, the catalyst (25) was subjected to X-ray diffractometry to measure its peak intensities; at d=4.00 Å and d=4.38 Å, i.e. $d_{4.00}$ and $d_{4.38}$; and the latter peak intensity was reported in Table 9 as relative peak intensity when the former peak intensity was taken as 100.

Comparative Example 15

A catalyst (26) having the same composition as that of the catalyst (25) was prepared in the same manner as in Example 28 except that ammonium meta-vana-date and antimony trichloride were used as they were, without being made into a V-Sb complex. Using the catalyst (26), an oxidation reaction was conducted under the same conditions as in Example 28. The results are shown in Table 9.

Separately, the catalyst (26) was subjected to X-ray diffractometry in the same manner as in Example 28 to measure its peak intensities at d=4.00 Å and d=4.38 Å, i.e. $d_{4.00}$ and $d_{4.38}$; and they were reported in Table 9 as relative peak intensities when the peak intensity of the catalyst (25) at d=4.00 Å was taken as 100.

Comparative Example 16

A catalyst (27) was prepared in the same manner as in Example 28 except that antimony pentachloride was used in place of the antimony trichloride used in Example 28 in production of a V-Sb complex. Using the catalyst (27), an oxidation reaction was conducted under the same conditions as in Example 28. The results are shown in Table 9.

Separately, the catalyst (27) was subjected to X-ray diffractometry in the same manner as in Example 28 to measure its peak intensities at d=4.00 Å and d=4.38 Å, i.e. $d_{4.00}$ and $d_{4.38}$; and they were reported in Table 9 as relative peak intensities when the peak intensity of the catalyst (25) at d=4.00 Å was taken as 100.

TABLE 9

| Example No. | Catalyst No. | Acrolein conversion (mole %) | Acrylic acid yield (mole %) | Acrylic acid selectivity (mole %) | Relative peak intensity | | |
|---|---|---|---|---|---|---|---|
| | | | | | $d_{4.00}$ | $d_{4.38}$ | $d_{4.38}/d_{4.00}$ |
| Example 28 | (25) | 98.8 | 94.6 | 95.8 | 100 | 1 | 0.01 |
| Comparative Example 15 | (26) | 92.5 | 87.4 | 94.5 | 84 | 6 | 0.07 |
| Comparative Example 16 | (27) | 96.0 | 89.7 | 93.4 | 87 | 12 | 0.14 |

EXAMPLE 29

An oxidation reaction was conducted for 4,000 hours using the catalyst (25) under the same conditions as in Example 28. Then, the product was collected and analyzed. The results are shown in Table 10.

The used catalyst (25) after 4,000-hour reaction was subjected to X-ray diffractometry to measure its peak intensity at d=4.00 Å, and it was reported in Table 10 as relative peak intensity at d=4.00 Å when the peak intensity of the unused catalyst (25) at d=4.00 Å was taken as 100.

Comparative Example 17

An oxidation reaction was conducted in the, same manner as in Example 29 except that the catalyst (26) was used in place of the catalyst (25). The results are shown in Table 10.

The used catalyst (26) after 4,000-hour reaction was subjected to X-ray diffractometry to measure its peak intensity at d=4.00 Å, and it was reported in Table 10 as relative peak intensity at d=4.00 Å when the peak intensity of the unused catalyst (25) at d=4.00 Å was taken as 100.

Comparative Example 18

An oxidation reaction was conducted in the same manner as in Example 29 except that the catalyst (27) was used in place of the catalyst (25). The results are shown in Table 10.

The used catalyst (27) after 4,000-hour reaction was subjected to X-ray diffractometry to measure its peak intensity at d=4.00 Å, and it was reported in Table 10 as relative peak intensity at d=4.00 Å when the peak intensity of the unused catalyst (25) at d=4.00 Å was taken as 100.

TABLE 10

| Example No. | Catalyst No. | Acrolein conversion (mole %) | Acrylic acid yield (mole %) | Acrylic acid selectivity (mole %) | Relative peak intensity at d = 4.00 Å |
|---|---|---|---|---|---|
| Example 29 | (25) | 98.0 | 93.7 | 95.6 | 96 |
| Comparative Example 17 | (26) | 90.9 | 86.0 | 94.6 | 75 |
| Comparative Example 18 | (27) | 94.5 | 88.3 | 93.4 | 79 |

EXAMPLE 30

An oxidation reaction was conducted in the same manner as in Example 28 using the catalyst (25) except that the contact time was changed to 1.5 seconds. The results are shown in Table 11.

Comparative Example 19

An oxidation reaction was conducted in the same manner as in Example 30 except that the catalyst (26) was used in place of the catalyst (25). The results are shown in Table 11.

Comparative Example 20

An oxidation reaction was conducted in the same manner as in Example 30 except that the catalyst (27) was used in place of the catalyst (25). The results are shown in Table 11.

EXAMPLE 31

An oxidation reaction was conducted in the same manner as in Example 28 using the catalyst (25) except that the proportions of acrolein and nitrogen in raw material gas were changed to 5% by volume and 65.5% by volume, respectively. The results are shown in Table 11.

Comparative Example 21

An oxidation reaction was conducted in the same manner as in Example 31 except that the catalyst (26) was used in place of the catalyst (25). The results are shown in Table 11.

Comparative Example 22

An oxidation reaction was conducted in the same manner as in Example 31 except that the catalyst (27) was used in place of the catalyst (25). The results are shown in Table 11.

TABLE 11

| Example No. | Catalyst No. | Acrolein conversion (mole %) | Acrylic acid yield (mole %) | Acrylic acid selectivity (mole %) |
|---|---|---|---|---|
| Example 30 | (25) | 98.6 | 94.2 | 95.5 |
| Comparative Example 19 | (26) | 92.0 | 86.9 | 94.5 |
| Comparative Example 20 | (27) | 95.5 | 89.0 | 93.2 |
| Example 31 | (25) | 98.5 | 93.8 | 95.2 |
| Comparative Example 21 | (26) | 91.7 | 86.4 | 94.2 |
| Comparative Example 22 | (27) | 95.3 | 88.4 | 92.8 |

EXAMPLE 32

[Preparation of V-Sb complex]

9.7 g of ammonium metavanadate was dissolved in 500 ml of water being heated and stirred. To the solution was added 25.4 g of antimony tetraoxide. The mixture was placed in a porcelain-made evaporator set on a hot water bath, and concentrated to dryness. The resulting solid was dried at 200° C. for 6 hours and then ground to obtain 35 g of a powder (A-2) of 150 μm or less. The powder (A-2) had the following metal composition.

$V_1Sb_2$

[Preparation of catalyst]

In 2,500 ml of water being heated and stirred were dissolved 350 g of ammonium paramolybdate, 106 g of ammonium metavanadate and 44.6 g of ammonium paratungstate. Thereto was added 35 g of the powder (A-2). Separately, 87.8 g of copper nitrate and 13 g of titanium oxide were added to 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (28). The catalyst (28) had the following metal composition.

$Mo_{12}V_6W_1Cu_{2.2}Sb_1Ti_1$

[Oxidation Reaction]

Using the catalyst (28), an oxidation reaction was conducted under the same conditions as in Example 28.

As a result, the acrolein conversion was 98.7%; the acrylic acid yield was 94.5%; and the acrylic acid selectivity was 95.7%. The ratio of peak intensities, i.e. $d_{4.38}/d_{4.00}$ was 0.03.

EXAMPLE 33

[Preparation of V-Sb complex]

4.8 g of ammonium metavanadate was dissolved in 500 ml of water being heated and stirred. To the solution was added 6 g of antimony trioxide. The mixture was placed in a porcelain-made evaporator set on a hot water bath, and concentrated to dryness. The resulting solid was dried at 350° C. for 6 hours and then ground to obtain a powder (A-3) of 150 µm or less. The powder (A-3) had the following metal composition.

$V_1Sb_1$

[Preparation of catalyst]

In 2,500 ml of water being heated and stirred were dissolved 350 g of ammonium paramolybdate, 101.5 g of ammonium metavanadate and 44.6 g of ammonium paratungstate. Thereto was added 10 g of the powder (A-3). Separately, 87.8 g of copper nitrate was dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (29). The catalyst (29) had the following metal composition.

$Mo_{12}V_{5.5}W_1Cu_{2.2}Sb_{0.25}$

[Oxidation reaction]

Using the catalyst (29), an oxidation reaction was conducted under the same conditions as in Example 28.

As a result, the acrolein conversion was 98.9%; the acrylic acid yield was 94.7%; and the acrylic acid selectivity was 95.8%. The ratio of peak intensities, i.e. $d_{4.38}/d_{4.00}$ was 0.03.

EXAMPLE 34

[Preparation of V-Sb complex]

19.3 g of ammonium metavanadate was dissolved in 500 ml of water being heated and stirred. To the solution were added 12.7 g of antimony tetraoxide and 6 g of antimony trioxide. The mixture was placed in a porcelain-made evaporator set on a hot water bath, and concentrated to dryness. The resulting solid was dried at 300° C. for 6 hours and then ground to obtain 33.5 g of a powder (A-4) of 150 µm or less. The powder (A-4) had the following metal composition.

$V_4Sb_3$

[Preparation of catalyst]

In 2,500 ml of water being heated and stirred were dissolved 350 g of ammonium paramolybdate, 96.6 g of ammonium metavanadate and 44.6 g of ammonium paratungstate. Thereto was added 33.5 g of the powder (A-4). Separately, 87.8 g of copper nitrate and 10.2 g of zirconium oxide were added to 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (30). The catalyst (30) had the following metal composition.

$Mo_{12}V_6W_1Cu_{2.2}Sb_{0.75}Zr_{0.5}$

[Oxidation reaction]

Using the catalyst (30), an oxidation reaction was conducted under the same conditions as in Example 28.

As a result, the acrolein conversion was 99%; the acrylic acid yield was 94.6%; and the acrylic acid selectivity was 95.6%. The ratio of peak intensities, i.e. $d_{4.38}/d_{4.00}$ was 0.04.

EXAMPLE 35

[Preparation of V-Sn complex]

38.7 g of ammonium metavanadate was dissolved in 500 ml of water being heated and stirred. To the solution was added 25 g of stannous hydroxide. The mixture was placed in a porcelain-made evaporator set on a hot water bath, and concentrated to dryness. The resulting solid was dried at 400° C. for 6 hours and then ground to obtain 52 g of a powder (A-5) of 150 µm or less. The powder (A-5) had the following metal composition.

$V_2Sn_1$

[Preparation of Catalyst]

In 2,500 ml of water being heated and stirred were dissolved 350 g of ammonium paramolybdate, 87 g of ammonium metavanadate and 44.6 g of ammonium paratungstate. Thereto was added 52 g of the powder (A-5). Separately, 87.8 g of copper nitrate was dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to ad here the above compounds onto the carrier, followed by firing at 400° C. for 6 hours, to obtain a catalyst (31). The catalyst (31) had the following metal composition.

$Mo_{12}V_{6.5}W_1Cu_{2.2}Sn_1$

[Oxidation reaction]

Using the catalyst (31), an oxidation reaction was conducted under the same conditions as in Example 28.

As a result, the acrolein conversion was 99.0%; the acrylic acid yield was 94.0%; and the acrylic acid selectivity was 95.0%. The ratio of peak intensities, i.e. $d_{4.38}/d_{4.00}$ was 0.05.

EXAMPLE 36

[Preparation of V-(Sb-Sn) complex]

19.3 g of ammonium metavanadate was dissolved in 500 ml of water being heated and stirred. To the solution were added 18.8 g of antimony trichloride and 3 g of stannous chloride. The mixture was placed in a porcelain-made evaporator set on a hot water bath, and concentrated to dryness. The resulting solid was dried at 500° C. for 6 hours and then ground to obtain 27.5 g of a powder (A-6) of 150 µm or less. The powder (A-6) had the following metal composition.

$V_{10}Sb_5Sn_1$

[Preparation of catalyst]

In 2,500 ml of water being heated and stirred were dissolved 350 g of ammonium paramolybdate, 96.6 g of ammonium metavanadate and 44.6 g of ammonium paratungstate. Thereto was added 27.5 g of the powder (A-6). Separately, 87.8 g of copper nitrate was dissolved in 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (32). The catalyst (32) had the following metal composition.

$Mo_{12}V_6W_1Cu_{2.2}Sb_{0.5}Sn_{0.1}$

[Oxidation reaction]

Using the catalyst (32), an oxidation reaction was conducted under the same conditions as in Example 28.

As a result, the acrolein conversion was 99.2%; the acrylic acid yield was 94.5%; and the acrylic acid selectivity was 95.3%. The ratio of peak intensities, i.e. $d_{4.38}/d_{4.00}$ was 0.04.

EXAMPLE 37

[Preparation of V-Sn complex]

9.7 g of ammonium metavanadate was dissolved in 500 ml of water being heated and stirred. To the solution was added 12.6 g of stannous hydroxide. The mixture was placed in a porcelain-made evaporator set on a hot water bath, and concentrated to dryness. The resulting solid was dried at 300° C. for 6 hours and then ground to obtain 20 g of a powder (A-7) of 150 µm or less. The powder (A-7) had the following metal composition.

$V_1Sn_1$

[Preparation of catalyst]

In 2,500 ml of water being heated and stirred were dissolved 350 g of ammonium paramolybdate, 106 g of ammonium metavanadate and 44.6 g of ammonium paratungstate. Thereto was added 20 g of the powder (A-7). Separately, 87.8 g of copper nitrate and 5.6 g of stannous oxide were added to 750 ml of water being heated and stirred. The resulting two fluids were mixed and placed in a porcelain-made evaporator set on a hot water bath. Thereto was added 1,000 ml of a spherical α-alumina carrier having diameters of 3–5 mm. The mixture was evaporated to dryness with stirring to adhere the above compounds onto the carrier, followed by firing at 400° C. for 6 hours, to obtain a catalyst (33). The catalyst (33) had the following metal composition.

$Mo_{12}V_6W_1Cu_{2.2}Sn_{0.75}$

[Oxidation reaction]

Using the catalyst (33), an oxidation reaction was conducted under the same conditions as in Example 28.

As a result, the acrolein conversion was 98.8%; the acrylic acid yield was 94.0%; and the acrylic acid selectivity was 95.1%. The ratio of peak intensities, i.e. $d_{4.38}/d_{4.00}$ was 0.05.

EXAMPLE 38

Industrial propylene (purity: 94% or higher) was subjected to catalytic gas-phase oxidation in the presence of a molybdenum/bismuth-based catalyst to obtain a reaction mixture gas comprising 5% by volume of acrolein, 1.2% by volume of unreacted propylene and organic by-products, 4.5% by volume of oxygen, 20% by volume of steam and 69.3% by volume of a nitrogen-containing inert gas.

Successively, the reaction mixture gas was introduced into a reaction tube filled with the catalyst (25) and subjected to an oxidation reaction under the conditions of temperature=255° C. and contact time=2 seconds.

An acrolein conversion of 98.9%, an acrylic acid selectivity of 95.6% and an acrylic acid per-pass yield of 94.5% were obtained based on an assumption that the propylene, propane, acrylic acid, acetic acid, etc. present in the reaction mixture gas introduced into the reaction tube did not take part in the oxidation reaction.

The above results confirmed that the catalyst produced by the present invention maintained a high activity and could produce acrylic acid from acrolein stably at a high yield.

What is claimed is:

1. A process for producing acrylic acid by subjecting acrolein or an acrolein-containing gas to gas-phase oxidation with molecular oxygen or a molecular oxygen-containing gas in the presence of a molybdenum/vanadium-based oxide catalyst represented by the following general formula (I):

$$Mo_aV_bW_cCu_dX_eY_fZ_gO_h \qquad (I)$$

wherein Mo is molybdenum; V is vanadium; W is tungsten; Cu is copper; X is at least one element selected from antimony and tin; Y is at least one element selected from magnesium, calcium, strontium and barium; Z is at least one element selected from titanium, zirconium and cerium; O is oxygen; a, b, c, d, e, f, g and h are the atom numbers of Mo, V, W, Cu, X, Y and Z, respectively, with a proviso that when a is 12, $2 \leq b \leq 14$, $0 \leq c \leq 12$, $0 < d \leq 6$, $0 \leq e \leq 5$, $0 \leq f \leq 3$ and $0 \leq g \leq 10$; and h is a number determined by the oxidation states of the individual elements other than O, in which process the molybdenum/vanadium-based oxide catalyst is produced by using the following substances as the raw materials of vanadium, copper, antimony and tin: when the molybdenum/vanadium-based oxide catalyst contains neither antimony nor tin, that is, when e=0, (A) the raw materials of vanadium are ammonium metavanadate and at least one vanadium oxide in which the valency of vanadium is larger than 0 but smaller than 5, and the raw material of copper is copper nitrate, or (B) the raw material of vanadium is ammonium metavanadate, and the raw materials of copper are copper nitrate and at least one copper oxide in which the valency of copper is larger than 0 but smaller than 2, or (C) the raw materials of vanadium are ammonium metavanadate and at least one vanadium oxide in which the valency of vanadium is larger than 0 but smaller than 5, and the raw materials of copper are copper nitrate and at least one copper oxide in which the valency of copper is larger than 0 but smaller than 2; and when the molybdenum/vanadium-based oxide catalyst contains antimony and/or tin, that is, when $0 < e \leq 5$, (D) the raw materials of vanadium are ammonium metavanadate and at least one vanadium oxide in which the valency of vanadium is larger than 0 but smaller than 5, the raw material of copper is copper nitrate, and at least part of the raw material(s) of antimony is at least one antimony oxide in which the valency of antimony is larger than 0 but smaller than 5, or (E) the raw materials of vanadium are ammonium metavanadate and at least one vanadium oxide in which the valency of vanadium is larger than 0 but smaller than 5, the raw material of copper is copper nitrate, and at least part of the raw material(s) of tin is at least one tin oxide in which the valency of tin is larger than 0 but smaller than 4, or (F) the raw materials of vanadium are ammonium metavanadate and at least one vanadium oxide in which the valency of vanadium is larger than 0 but smaller than 5, the raw material of copper is copper nitrate, at least part of the raw material(s) of antimony is at least one antimony oxide in which the valency of antimony is larger than 0 but smaller than 5, and at east part of the raw material(s) of tin is at least one tin oxide in which the valency of tin is larger than 0 but smaller than 4, or (G) the raw material of vanadium is ammonium metavanadate, the raw materials of copper are copper nitrate and at least one copper oxide in which the valency of copper is larger than 0 but smaller than 2, and at least part of the raw material(s) of antimony is at least one antimony oxide in which the valency of antimony is larger than 0 but smaller than 5, or (H) the raw material of vanadium is ammonium metavanadate, the raw materials of copper are copper nitrate and at least one copper oxide in which the valency of copper is larger than 0 but smaller than 2, and at least part of the raw material(s) of tin is at least one tin oxide in which the valency of tin is larger than 0 but smaller than 4, or (I) the raw material of vanadium is ammonium metavanadate, the raw materials of copper are copper nitrate and at least one copper oxide in which the valency of copper is larger than 0 but smaller than 2, at least part of the raw material(s) of antimony is at least one antimony oxide in which the valency of antimony is larger than 0 but smaller than 5, and at least part of the raw material(s) of tin is at least one tin oxide in which the valency of tin is larger than 0 but smaller than 4, or (J) the raw materials of vanadium are ammonium metavanadate and at least one vanadium oxide in which the valency of vanadium is larger than 0 but smaller than 5, the raw materials of copper are copper nitrate and at least one copper oxide in which the valency of copper is larger than 0 but smaller than 2, and at least part of the raw material(s) of antimony is at least one antimony oxide in which the valency of antimony is larger than 0 but smaller than 5, or (K) the raw materials of vanadium are ammonium metavanadate and at least one vanadium oxide, in which the valency of vanadium is larger than 0 but smaller than 5, the raw materials of copper are copper nitrate and at least one copper oxide in which the valency of copper is larger than 0 but smaller than 2, and at least part of the raw material(s) of tin is at least one tin oxide in which the valency of tin is larger than 0 but smaller than 4, or (L) the raw materials of vanadium are ammonium metavanadate and at least one vanadium oxide in which the valency of vanadium is larger than 0 but smaller than 5, the raw materials of copper are copper nitrate and at least one copper oxide in which the valency of copper is larger than 0 but smaller than 2, at least part of the raw material(s) of antimony is at least one antimony oxide in which the valency of antimony is larger than 0 but smaller than 5, and at least part of the raw material(s) of tin is at least one tin oxide in which the valency of tin is larger than 0 but smaller than 4, or (M) the raw material of vanadium is ammonium metavanadate and part thereof is used in the form of a complex with an antimony compound in which the valency of antimony is larger than 0 but smaller than 5, and the raw material of copper is copper nitrate, or (N) the raw material of vanadium is ammonium metavanadate and part thereof is used in the form of a complex with a tin compound in which the valency of tin is larger than 0 but smaller than 4, and the raw material of copper is copper nitrate, or (O) the raw material of vanadium is ammonium metavanadate and part thereof is used in the form of a complex with (1) an antimony compound in which the valency of antimony is larger than 0 but smaller than 5 and (2) a tin compound in which the valency of tin is larger than 0 but smaller than 4, and the raw material of copper is copper nitrate.

2. A process according to claim 1, wherein the catalyst is supported on an inactive carrier.

3. A process according to claim 1 or 2, wherein the oxidation reaction is carried out by contacting, with the catalyst, a mixed gas comprising 1–15% by volume of acrolein, 0.5–25% by volume of oxygen, 0–30% by volume of steam and 20–80% by volume of an inert gas at a temperature of 180°–350° C. at a pressure of normal pressure to 10 atm. at a space velocity (STP) of 500–20,000 hr$^{-1}$.

4. A process according to claim 1 or 2, wherein the oxidation reaction is carried out by contacting, with the catalyst, a mixed gas comprising 4–12% by volume of acrolein, 2–20% by volume of oxygen, 3–25% by volume of steam and 50–70% by volume of an inert gas at a temperature of 200°–330° C. at a pressure of normal pressure to 10 arm. at a space velocity (STP) of 1,000–10,000 h$^{-1}$.

5. A process according to claim 1, wherein the catalyst, when subjected to X-ray diffractometry, gives a ratio of peak intensity at d=4.38 Å to peak intensity at d=4.00 Å, of less than 0.07.

6. A process according to claim 1, wherein the catalyst has a peak intensity retention of at least 80% when the peak intensity retention is defined as percent of the peak intensity at d=4.00 Å, of used catalyst after 4000-hour operation to the peak intensity at d=4.00 Å, of unused catalyst when the two catalysts are subjected to X-ray diffractometry.

7. Process according to claim 1, wherein the d in $Cu_d$ is 0.01 to 6 and the e in $X_e$ is 0.01 to 5, provided however that Sb and Sn halides are not used in the preparation of the catalyst, except when they are used in the formation of a V-Sb and V-Sn complex to prepare the catalyst.

8. Process according to claim 5, wherein the d in $Cu_d$ is 0.01 to 6 and the e in $X_e$ is 0.01 to 5, provided however that Sb and Sn halides are not used in the preparation of the catalyst, except when they are used in the formation of a V-Sb and V-Sn complex to prepare the catalyst.

9. A process according to claim 1, wherein the d in $Cu_d$ is 0.01 to 6 and the e $X_e$ is 0.01 to 5 and the g in Zg is 0, provided however that Sb and Sn halides are not used in the preparation of the catalyst, except when they are used in the formation of a V-Sb and V-Sn complex to prepare the catalyst.

10. A process according to claim 5, wherein the d in $Cu_d$ is 0.01 to 6 and the e $X_e$ is 0.01 to 5 and the g in $Z_g$ is 0, provided however that the Sb and Sn halides are not used in the preparation of the catalyst, except when they are used in the formation of a V-Sb and V-Sn complex to prepare the catalyst.

11. A process for producing acrylic acid by subjecting acrolein or an acrolein-containing gas to gas-phase oxidation with molecular oxygen or a molecular oxygen-containing gas in the presence of a molybdenum/vanadium-based oxide catalyst represented by the following general formula (I):

$$Mo_aV_bW_cCu_dX_eY_fZ_gO_h \qquad (I)$$

wherein Mo is molybdenum; V is vanadium; W is tungsten; Cu is copper; X is at least one element selected from antimony and tin; Y is at least one element selected from magnesium, calcium, strontium and barium; Z is at least one element selected from titanium, zirconium and cerium; O is oxygen; a, b, c, d, e, f, g and h are the atom numbers of Mo, V, W, Cu, X, Y and Z, respectively, with a proviso that when a is 12, $2 \leq b \leq 14$, $0 \leq c \leq 12$, $0 < d \leq 6$, $0 \leq e \leq 5$, $0 \leq f \leq 3$ and $0 \leq g \leq 10$; and h is a number determined by the oxidation states of the individual elements other than O, in which process the molybdenum/vanadium-based oxide catalyst is produced by using the following substances as the raw materials of vanadium, copper, antimony and tin: when the molybdenum/vanadium-based oxide catalyst contains neither antimony nor tin, that is, when e=0, provided however that Sb and Sn halides are not used in the preparation of the catalyst, except when they are used in V-Sb and V-Sn complexes, (A) the raw materials of vanadium are ammonium metavanadate and an effective amount of at least one vanadium oxide in which the valency of vanadium is larger than 0 but smaller than 5, and
the raw material of copper is copper nitrate, or (B) the raw material of vanadium is ammonium metavanadate, and
the raw materials of copper are copper nitrate and an effective amount at least one copper oxide in which the valency of copper is larger than 0 but smaller than 2, or (C) raw materials of vanadium are ammonium metavanadate and an effective amount of at least one vanadium oxide in which the valency of vanadium is larger than 0 but smaller than 5, and
the raw materials of copper are copper nitrate and an effective amount of at least one copper oxide in which the valency of copper is larger than 0 but smaller than 2; and when the molybdenum/vanadium-based oxide catalyst contains antimony and/or tin, that is , when $0 < e \leq 5$, (D) the raw materials of vanadium are ammonium metavanadate and an effective amount of at least one vanadium oxide in which the valency of vanadium is larger than 0 but smaller than 5,
the raw material of copper is copper nitrate, and
at least part of the raw material(s) of antimony is an effective amount of at least one antimony oxide in which the valency of antimony is larger than 0 but smaller than 5, or (E) the raw materials of vanadium are ammonium metavanadate and an effective amount of at least one vanadium oxide in which the valency of vanadium is larger than 0 but smaller than 5,
the raw material of copper is copper nitrate, and at least part of the raw material(s) of tin is an effective amount of at least one tin oxide in which the valency of tin is larger than 0 but smaller than 4, or (F) the raw materials of vanadium are ammonium metavanadate and an effective amount if at least one vanadium oxide in which the valency of vanadium is larger than 0 but smaller than 5,
the raw material of copper is copper nitrate, at least part of the raw material(s) of antimony is an effective amount of at least one antimony oxide in which the valency of antimony is larger than 0 but smaller than 5, and
at lease part of the raw material(s) of tin is an effective amount of at least one tin oxide in which the valency of tin is larger than 0 but smaller than 4, or (G) the raw material of vanadium is ammonium metavanadate,
the raw materials of copper are copper nitrate and an effective amount of at least one copper oxide in which the valency of copper is larger than 0 but smaller than 2, and
at least part of the raw material(s) of antimony is an effective amount of at least one antimony oxide in which the valency of antimony is larger than 0 but smaller than 5, or (H) the raw material of vanadium is ammonium metavanadate,
the raw materials of copper are copper nitrate and an effective amount of at least one copper oxide in which the valency of copper is larger than 0 but smaller than 2, and
at least part of the raw material(s) of tin is an effective amount of at least one tin oxide in which the valency of tin is larger than 0 but smaller than 4, or (I) the raw material of vanadium is ammonium metavanadate,
the raw materials of copper are copper nitrate and at least one copper oxide in which the valency of copper is larger than 0 but smaller than 2,
at least part of the raw material(s) of antimony is an effective amount of at least one antimony oxide in which the valency of antimony is larger than 0 but smaller than 5, and
at least part of the raw material(s) of tin is at an effective amount of at least one tin oxide in which the valency of tin is larger than 0 but smaller than 4, of (J) the raw materials of vanadium are ammonium metavanadate and an effective amount of at least one vanadium oxide in which the valency of vanadium is larger than 0 but smaller than 5,
the raw materials of copper are copper nitrate and an effective amount of at least one copper oxide in which the valency of copper is larger than 0 but smaller than 2, and
at least part of the raw material(s) of antimony is an effective amount of at least one antimony oxide in which the valency of antimony is larger than 0 but smaller than 5, or (K) the raw materials of vanadium are ammonium metavanadate and an effective amount of at least one vanadium oxide in which the valency of vanadium is larger than 0 but smaller than 5,
the raw materials of copper are copper nitrate and an effective amount of at least one copper oxide in which the valency of copper is larger than 0 but smaller than 2, and
at least part of the raw material(s) of tin is an effective amount of at least one tin oxide in which the valency of tin is larger than 0 but smaller than 4, or (L) the raw materials of vanadium are ammonium metavanadate and an effective amount of at least one vanadium oxide in which the valency of vanadium is larger than 0 but smaller than 5, the raw materials of copper are copper nitrate and an effective amount of at least one copper oxide in which the valency of copper is larger than 0 but smaller than 2, an effective amount of at least part of the raw material(s) of antimony is at least one antimony oxide in which the valency of antimony is larger than 0 but smaller than 5, and an effective amount of at least part of the raw material(s) of tin is at least one tin oxide in which the valency of tin is larger than 0 but smaller than 4, or (M) the raw material of vanadium is ammonium metavanadate and part thereof is used in the form of an effective amount of a complex with an antimony compound in which the valency of antimony is larger than 0 but smaller than 5, and the raw material of copper is copper nitrate, or (N) the raw material of vanadium is ammonium metavanadate and part thereof is used in the form of an effective amount of a complex with a tin compound in which the valency of ten is larger than 0 but smaller than 4, and the raw material of copper is copper nitrate, or (O) the raw material of vanadium is ammonium metavanadate and part thereof is used in the form of an effective amount of a complex with (1) an antimony compound in which the valency of antimony is larger than 0 but smaller than 5 and (2) an effective amount of a tin compound in which the valency of tin is larger than 0 but smaller than 4, and the raw material of copper is copper nitrate.

12. Process according to claim 11, wherein the d in $Cu_d$ is 0.01 to 6 and the e in $X_e$ is 0.01 to 5.

13. A process according to claim 11, wherein the d in $Cu_d$ is 0.01 to 6 and the e $X_e$ is 0.01 to 5 and the g in Zg is 0.

* * * * *